(12) United States Patent
Kapiamba

(10) Patent No.: US 8,450,529 B2
(45) Date of Patent: May 28, 2013

(54) BRANCHED POLYAMINES AND FORMULATIONS THEREOF FOR USE IN MEDICAL DEVICES

(75) Inventor: Mbiya Kapiamba, Cromwell, CT (US)

(73) Assignee: Covidien LP, Mansfield, MA (US)

( * ) Notice: Subject to any disclaimer, the term of this patent is extended or adjusted under 35 U.S.C. 154(b) by 853 days.

(21) Appl. No.: 12/502,723

(22) Filed: Jul. 14, 2009

(65) Prior Publication Data

US 2010/0087668 A1   Apr. 8, 2010

Related U.S. Application Data

(60) Provisional application No. 60/102,041, filed on Oct. 2, 2008.

(51) Int. Cl.
*C07C 209/00* (2006.01)

(52) U.S. Cl.
USPC ............................................. 564/423

(58) Field of Classification Search
None
See application file for complete search history.

(56) References Cited

U.S. PATENT DOCUMENTS

| | | | |
|---|---|---|---|
| 2,830,008 A | 4/1958 | Barber et al. | |
| 3,081,302 A | 3/1963 | Shapiro et al. | |
| 3,843,647 A | 10/1974 | Buzas et al. | |
| 4,051,259 A | 9/1977 | Buzas et al. | |
| 4,435,548 A | 3/1984 | Tomalia et al. | |
| 4,472,568 A | 9/1984 | Rasshofer et al. | |
| 4,507,466 A | 3/1985 | Tomalia et al. | |
| 4,515,923 A | 5/1985 | Fauss et al. | |
| 4,525,534 A | 6/1985 | Rasshofer | |
| 4,540,720 A | 9/1985 | Rasshofer et al. | |
| 4,558,120 A | 12/1985 | Tomalia et al. | |
| 4,565,645 A | 1/1986 | Rasshofer et al. | |
| 4,568,737 A | 2/1986 | Tomalia et al. | |
| 4,587,329 A | 5/1986 | Tomalia et al. | |
| 4,599,400 A | 7/1986 | Tomalia et al. | |
| 4,631,337 A | 12/1986 | Tomalia et al. | |
| 4,690,985 A | 9/1987 | Tomalia et al. | |
| 4,723,032 A | 2/1988 | Rasshofer et al. | |
| 4,737,550 A | 4/1988 | Tomalia | |
| RE32,677 E | 5/1988 | Rasshofer et al. | |
| 4,857,599 A | 8/1989 | Tomalia et al. | |
| 4,931,595 A | 6/1990 | Rasshofer | |
| 4,970,342 A | 11/1990 | Fauss et al. | |
| 5,418,301 A | 5/1995 | Hult et al. | |
| 5,631,329 A | 5/1997 | Yin et al. | |
| 5,646,236 A | 7/1997 | Schafheutle et al. | |
| 5,859,148 A | 1/1999 | Borggreve et al. | |
| 6,072,023 A | 6/2000 | Sato et al. | |
| 6,184,197 B1 | 2/2001 | Heinzman et al. | |
| 2006/0079599 A1 | 4/2006 | Arthur | |
| 2006/0128608 A1 | 6/2006 | Cianci et al. | |
| 2006/0172983 A1* | 8/2006 | Bezwada ............... 514/165 | |
| 2007/0031371 A1* | 2/2007 | McManus et al. ........ 424/78.37 | |
| 2010/0209380 A1* | 8/2010 | Kapiamba et al. ........ 424/78.06 | |

FOREIGN PATENT DOCUMENTS

| | | | |
|---|---|---|---|
| EP | 0810203 | | 4/1997 |
| JP | 63 250350 A | | 10/1988 |
| JP | 02 163121 A | | 6/1990 |
| JP | 02 166121 A | | 6/1990 |
| JP | 02 263828 A | | 10/1990 |
| WO | WO 2004/050677 | | 6/2004 |
| WO | WO2005113487 | * | 5/2005 |
| WO | WO 2005/075527 | | 8/2005 |
| WO | WO 2007/033418 | | 3/2007 |

OTHER PUBLICATIONS

Peppas et al. European Journal of Pharmaceutics and Biopharmaceuticals 50 (2000) 27-46.*
March, J. "Advanced Organic Synthesis", 4th edition, 1992, pp. 205 and 903).*
European Search Report for EP 09252351.3 date of completion is Feb. 22, 2010 (3 pages).

* cited by examiner

*Primary Examiner* — Sudhakar Katakam
*Assistant Examiner* — Clinton Brooks

(57) ABSTRACT

The present disclosure provides for the synthesis of branched polyamines. In embodiments, branched polyamines may be formed by reacting a branched polyol with a nitroaryl carboxylic acid to form a nitrobenzoyl ester which, in turn, may then be subjected to a hydrogenating step to form the branched polyamine. The resulting branched polyamine may then be reacted with another hydrogel precursor to form a hydrogel.

22 Claims, No Drawings

BRANCHED POLYAMINES AND FORMULATIONS THEREOF FOR USE IN MEDICAL DEVICES

CROSS-REFERENCE TO RELATED APPLICATIONS

This application claims the benefit of and priority to U.S. Provisional Patent Application No. 60/102,041, filed Oct. 2, 2008, the entire disclosure of which is incorporated by reference herein.

BACKGROUND

The present disclosure provides methods for the synthesis of branched polyamines and their use as cross-linkers in conjunction with various polymeric compounds to form useful medical compounds.

Synthetic biocompatible materials have multiple applications in the medical field and are used as sealants, adhesives, tissue repair devices (e.g., tissue engineering scaffolds) and/or drug delivery devices. Biocompatible polymers may be either bioabsorbable or biostable. A bioabsorbable polymer breaks down in the body via hydrolysis, metabolic processes, bulk erosion, or surface erosion. Physical and chemical properties e.g., melting point, degradation rate, stiffness, etc., of such materials can vary with the use different polymeric materials. The variability in physical and chemical properties allows products made from such materials to be tailored to suit specific applications.

Bioabsorbable polymers may be synthesized from a variety of precursor compounds. Due, in part, to the variability of both the polymers and precursors utilized to produce such polymers, there is a continual need to provide for efficient and cost-effective ways to synthesize desirable precursors and polymers prepared therefrom.

SUMMARY

The present disclosure provides methods for producing branched polyamines. These polyamines, in turn, may be used as cross-linkers with various polymeric compounds to form useful medical compounds. In embodiments, a process of the present disclosure may include reacting a branched polyol with a nitroaryl carboxylic acid to form a nitrobenzoyl ester, and hydrogenating the nitrobenzoyl ester to form a branched polyamine.

In other embodiments, a process of the present disclosure may include reacting a branched polyol with a nitroaryl carboxylic acid to form a nitrobenzoyl ester, and reducing the nitrobenzoyl ester with a catalyst to form a branched polyamine.

Other processes of the present disclosure may include reacting a branched polyol with a nitroaryl carboxylic acid to form a nitrobenzoyl ester, hydrogenating the nitrobenzoyl ester to form a branched polyamine, and reacting the branched polyamine with a hydrogel precursor.

In some embodiments, the branched polyamine may be contacted with a protected amino acid comprising tert-butoxycarbonyl glycine,

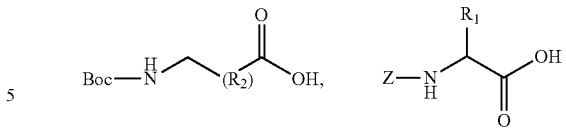

and combinations thereof to form a protected polyamine, followed by contacting the protected polyamine with an acid such as trifluoroacetic acid (TFA), HCl in dioxane, and combinations thereof to form an aliphatic component, wherein $R_1$ may be alkyl, aryl, heteroaryl, cycloalkyl, and substituted derivatives thereof, $R_2$ may be $CH_2$, alkyl, alkyloxy, and combinations thereof, and Z may be tert-butoxycarbonyl, benzyloxycarbonyl, and fluorenylmethyoxycarbonyl.

DETAILED DESCRIPTION

The present disclosure relates to processes for the production of branched polyamines suitable for use in the formation of biocompatible and/or biodegradable polymers.

In embodiments, branched polyamines may be formed from polyols. Any polyol may be utilized as a starting material. Suitable polyols may be any compound with multiple hydroxyl groups, such as a diol, a triol, a tetrol and the like. In embodiments, the polyol may be a branched polyol of various molecular weights. As used herein, "branched" denotes a chain of atoms with one or more side chains attached to it. Branching occurs by the replacement of a substituent, e.g., a hydrogen atom, with a covalently bonded substituent or moiety, e.g., an alkyl group, an aryl group, or combination thereof. The branched polyol may also include various alkoxy groups as one of the branches, such as ethoxylate, propoxylate, and the like.

In embodiments, the branched polyol useful as a reagent for preparing the branched polyamine may have at least 4 carbon atoms and at least 3 hydroxyl groups. Non-limiting examples of trifunctional, tetrafunctional or higher polyols suitable for use as the branched polyol include branched chain alkane polyols such as glycerol or glycerin, tetramethylolmethane, trimethylolethane (for example 1,1,1-trimethylolethane), trimethylolpropane (TMP) (for example 1,1,1-trimethylolpropane), caprolactone, glucose, sorbitol, erythritol, pentaerythritol, dipentaerythritol, tripentaerythritol, sorbitan, alkoxylated derivatives thereof (discussed below) and combinations thereof. Suitable branched pentaerythritols may include pentaerythritol ethoxylate and pentaerythritol propoxylate, combinations thereof, and the like.

The polyol, in embodiments a branched polyol, may be reacted with a carboxylic acid having a nitrogen group through an esterification reaction to form a nitro ester. The acid may be any type of carboxylic acid, such as a nitroaryl carboxylic acid wherein the nitro group of the carboxylic acid is a nitroaromatic group. Suitable carboxylic acids include, for example, 3-nitrobenzoic acid, p-nitrophenoxyacetic acid, m-nitrophenoxyacetic acid, o-phenyl acetic acid, m-phenyl acetic acid, p-phenyl acetic acid, m,p-nitrocinnamyl acid, benzoic acid, and 4-nitrobenzoic acid. The esterification reaction may also include addition of an activating agent, such as oxalyl chloride, thionyl chloride and the like, and/or a coupling agent such as dicyclohexyl carbodiimide (DCC) or 1-ethyl-3-(3-dimethylaminopropyl)carbodiimide (EDC), and the like.

The resulting nitro ester may then undergo hydrogenation (e.g., reduction) of the resulting nitroaromatic functional groups to form nitroamine groups. In embodiments, the hydrogenation may be performed in the presence of a catalyst and a source of hydrogen. In embodiments, the catalyst may include a metal such as any of the so-called "platinum group"

metals including platinum, palladium, rhodium and/or ruthenium. In embodiments, these metal catalysts may be disposed on a carbon substrate. A suitable hydrogen source may be hydrogen gas supplied at a predetermined pressure, for example from about 14.7 psi to about 40 psi. The hydrogenation of the nitro esters forms corresponding branched polyamines.

Hydrogen can also be transferred to the nitro ester from hydrogen-donor molecules, such as hydrazine, ammonium formate, dihydronaphthalene, dihydroanthracene, isopropanol, cylcohexene, formic acid and the like. Hydrogen-donor molecules may be added to the reaction in an amount from about 5 molar equivalents of the nitro ester to about 20 molar equivalents of the nitro ester, in embodiments from about 8 molar equivalents of the nitro ester to about 10 molar equivalents of the nitro ester.

Thus, to summarize, the starting materials utilized to form the branched polyamines, for example the branched polyol described above, may be combined with the above nitroaryl carboxylic acid to initially form a branched nitro ester. The embodiments from about 5 grams to about 100 grams, the acid having a group may be added in amounts of from about 1 gram to about 1 kilogram, in embodiments from about 10 grams to about 250 grams; and the activating agent may be added in amounts of from about 1 to about 20 molar equivalents relative to the number of hydroxyl groups, in embodiments from about 1.5 to about 6 molar equivalents relative to the number of hydroxyl groups. The appropriate amount of starting materials may be dissolved in a solvent, optionally in combination with an oxalyl halide. Where utilized, suitable solvents include, but are not limited to, tetrahydrofuran, acetonitril, ethyl acetate and the like.

The reaction can also be carried out by mixing the polyol with nitrocarboxylic acid in the presence of coupling agents such as DCC, EDC, carbonyl diimidazole, or other coupling agents within the purview of those skilled in the art.

Exemplary syntheses of branched polyamines from various starting materials are depicted below. Esterfication of a branched polyol may proceed as follows:

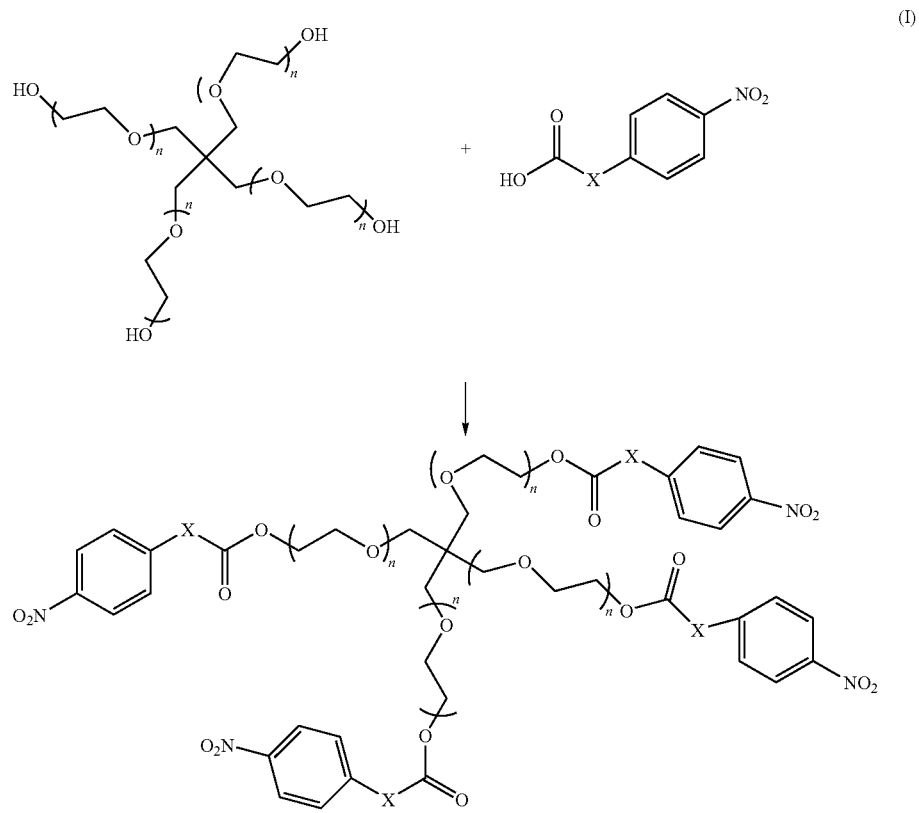

nitro ester is then hydrogenated to convert the nitroaromatic functional groups into the nitroamines, thereby forming a branched polyamine. The branched aromatic amine may be further reacted with a protected amino acid such as tert-butoxycarbonyl glycine to form a protected alkylamine. Deprotection of the amine may produce a more reactive polyalkylene linker.

Reaction Conditions

In the synthesis process, the reactants may be added to a suitable reactor, such as a mixing vessel. The amounts of the reactants may vary. In embodiments, the polyol may be added in amounts of from about 1 gram to about 16 kilograms, in where n is from about 0 to about 113, in embodiments from about 3 to about 50, and x may be carbon, $(CH_2)_y$, or $(CH_2)_yO$, where y is from about 1 to about 6, in embodiments from about 2 to about 4.

As shown by reaction (I), a branched polyol may be reacted with a nitroaryl carboxylic acid to form a nitro ester, such as a nitrophenyl ester. The nitrophenyl ester may then be hydrogenated in the presence of a platinum family catalyst to form a branched polyamine. In embodiments, the hydrogenation of the resulting branched nitro ester may proceed as follows:

(II)

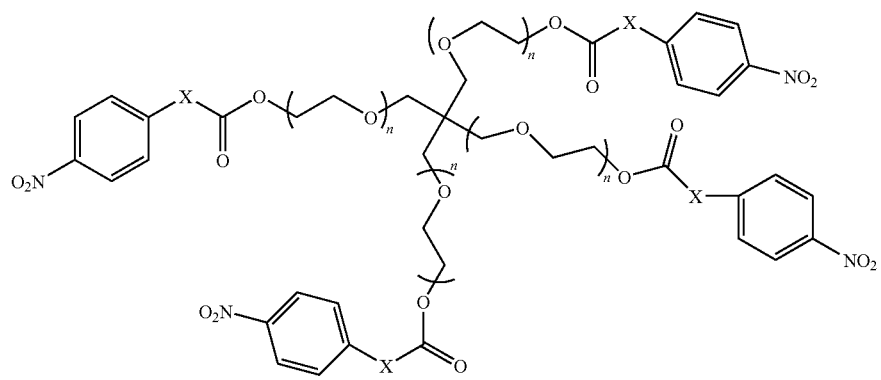

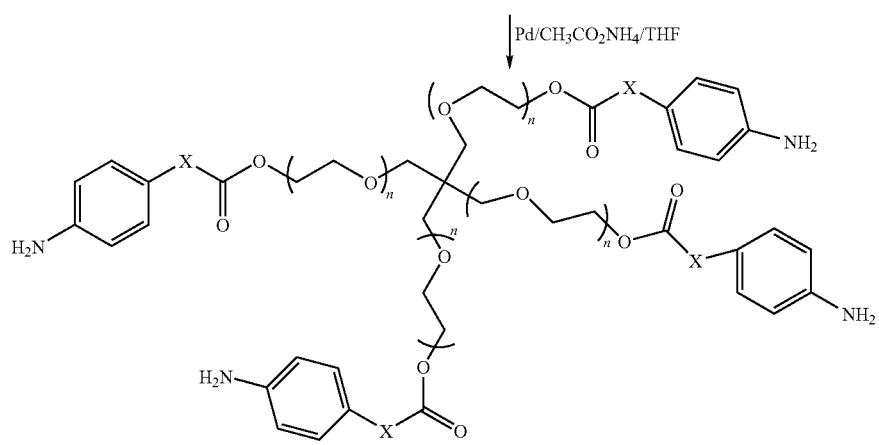

The time for the reaction may depend upon the type and amount of starting materials utilized, temperature, and the like. In embodiments, the reaction mixture may be mixed for from about 1 hour to about 72 hours, in embodiments for about 4 hours to about 20 hours, while keeping the temperature from about 50° C. to about 70° C., in embodiments from about 60° C. to about 65° C.

The resulting branched polyamine may have a molecular weight of from about 628 to about 50,000, in embodiments from about 700 to about 25,000.

The terminal aromatic amines can be further converted to aliphatic components by coupling the amine group with the carboxylic acid group of a N-protected amino acid such as tert-butoxycarbonyl (N-Boc) glycine, and combinations thereof to form a protected polyamine, followed by deprotection using acids such as trifluoroacetic acid (TFA), HCl in dioxane, and/or combinations thereof. Exemplary synthesis is as follows:

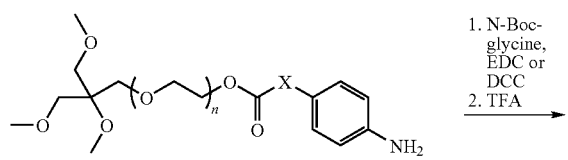

-continued

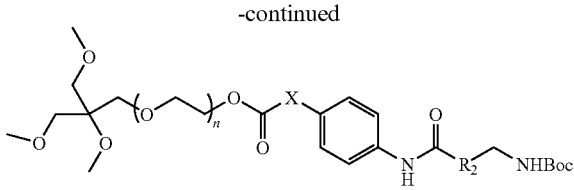

where $R_2$=$CH_2$, alkyl, alkyloxy, and combinations thereof

Other possible protected acids which may be utilized to form the aliphatic components include:

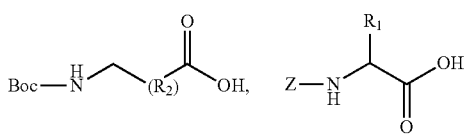

Protected α-amino acids where $R_1$=alkyl, substituted alkyl, cycloalkyl, substituted cycloalkyl, aryl, substituted aryl, heteroaryl, substituted heteroaryl;

where $R_2$=$CH_2$, alkyl, alkyloxy, and combinations thereof; and where Z=Boc (Benzyloxycarbonyl), Fmoc (fluorenylmethyoxycarbonyl), Ph (phenyl).

In embodiments, combinations of any of the foregoing acids may be utilized.

The resulting aliphatic components may include, in embodiments, the following:

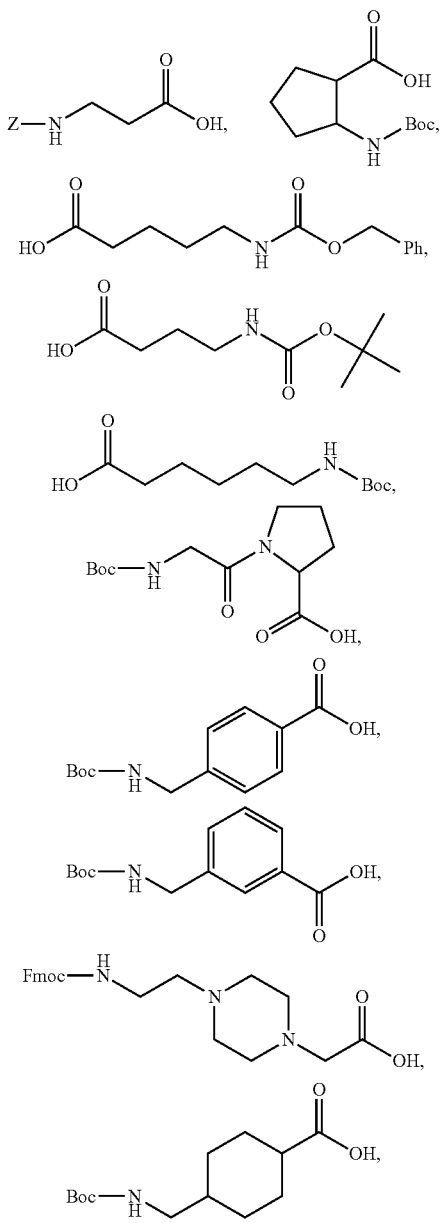

Other potential aliphatic components include:

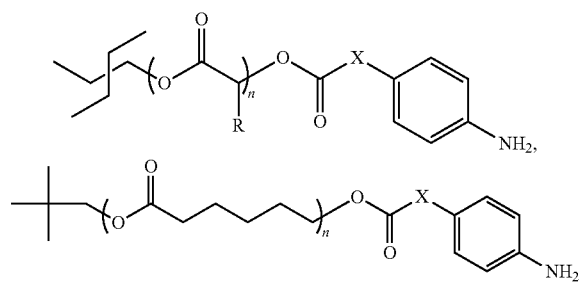

Applications

In embodiments, the branched polyamines produced according to the present disclosure as described above may find use in the formation of polymers which, in turn, may find use in medical applications. For example, the branched polyamines synthesized in accordance with the present disclosure may be used as cross-linkers in a reaction with another precursor, in embodiments a matrix-forming hydrogel precursor, to form a hydrogel. As used herein, a "hydrogel precursor" includes any component reacted with a branched polyamine described above to form a hydrogel. In embodiments, branched polyamines may be reacted with a matrix forming hydrogel precursors such as carboxylic acids, aldehydes and other monomeric or polymeric precursor materials, such as with polycarboxylic acids and polyaldehydes, to form hydrogels and other compounds for use as medical sealants or adhesives as well as tissue-repair and drug delivery devices.

In embodiments, a hydrogel precursor reacted with the branched polyamines described above may be a macromolecule, sometimes referred to herein as a "functional polymer". In embodiments, the hydrogel precursors may contain multiple electrophilic groups, and thus may be referred to herein as "multi-electrophilic precursors." The multi-electrophilic precursor may contain at least two, in embodiments at least three, electrophilic groups in order to form a three-dimensional crosslinked network with the branched polyamines described above.

The hydrogel precursor may have a molecular weight of from about 500 to about 5000, in embodiments from about 800 to about 2000.

Thus, the hydrogel precursor may be from at least about 2 to about 40 times greater in molecular weight than the branched polyamine, in embodiments from at least about 10 to about 30 times greater in molecular weight than the branched polyamine.

Since the branched polyamines of the present disclosure include nucleophilic functional groups, i.e., their terminal amines, in embodiments the other hydrogel precursor may include one or more electrophilic functional groups, such as carbonylimidazole, sulfonyl chloride, chlorocarbonates, n-hydroxysuccinimidyl esters, succinimidyl esters, sulfosuccinimidyl esters, phenolic esters, and combinations thereof. In embodiments, the hydrogel precursor has electrophilic functional groups such as N-hydroxysuccinimides.

The hydrogel precursors may have biologically inert and water soluble cores. When the core is a polymeric region that is water soluble, suitable polymers that may be used include, but are not limited to, polyethers, for example, polyalkylene oxides such as polyethylene glycol ("PEG"), polyethylene oxide ("PEO"), polypropylene oxide ("PPO"), polyethylene oxide-co-polypropylene oxide, co-polyethylene oxide block or random copolymers, and polyvinyl alcohol ("PVA"); poly (vinyl pyrrolidinone) ("PVP"); poly (saccharides), such as dextran, chitosan, alginates, carboxymethylcellulose, oxidized cellulose, hydroxymethylcellulose, hydroxymethylcellulose, hyaluronic acid. The polyethers and more particularly poly(oxyalkylenes) or polyethylene glycol may be especially useful. When the core is small in molecular nature, any of a variety of hydrophilic functionalities can be used to make the first and second hydrogel precursors water soluble. For example, solubilizing functional groups like hydroxyl, amine, sulfonate and carboxylate, which are water soluble, may be used to make the precursor water soluble.

If it is desired that the biocompatible crosslinked polymer resulting from the reaction of the branched polyamine and the hydrogel precursors be biodegradable or absorbable, either the branched polyamine or the hydrogel precursors may have biodegradable linkages present between the functional groups. The biodegradable linkage may also serve as a water solubilizing core of the branched polyamine or hydrogel precursors. In the alternative, or in addition, the functional groups of the hydrogel precursors may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. In embodiments, biodegradable linkages may be selected that degrade under physiological conditions into non-toxic products.

The biodegradable linkage may be chemically or enzymatically hydrolyzable or absorbable. Illustrative chemically hydrolyzable biodegradable linkages include polymers, copolymers and oligomers of glycolide, dl-lactide, 1-lactide, caprolactone, dioxanone, and trimethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s.

In embodiments, a multifunctional electrophilic polymer such as a multi-arm PEG functionalized with multiple NHS ester groups may be used as a hydrogel precursor. The multi-arm PEG functionalized with multiple NHS ester groups can have, for example, four, six or eight arms, and a molecular weight of from about 5,000 to about 25,000. Many other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated by reference herein.

Preparation of Crosslinked Compositions

In embodiments, the crosslinked polymer compositions described herein, in embodiments hydrogels, may be prepared by combining a branched polyamine with a hydrogel precursor containing multiple electrophilic groups. Formation of a three-dimensional crosslinked network occurs as a result of the reaction between the nucleophilic (amine) groups on the branched polyamine and the electrophilic groups on the hydrogel precursor.

Other nucleophilic functional polymers such as proteins, poly(allyl amine), styrene sulfonic acid, or amine-terminated di- or multifunctional poly(ethylene glycol) ("PEG") may be added to the branched polyamine and an electrophilic hydrogel precursor during formation of a hydrogel.

Crosslinking of the branched polyamine and hydrogel precursor may occur at temperatures of from about 20° C. to about 40° C., in embodiments from about 25° C. to about 35° C., for a period of time of from about 10 seconds to about 60 minutes, in embodiments from about 30 seconds to about 5 minutes. The exact reaction conditions may depend on a variety of factors, including the branched polyamines and hydrogel precursors utilized, their functionality, the degree of functionality, the presence of additives, if any, and the like.

The concentrations of the branched polyamine and the hydrogel precursor used to prepare the present compositions will vary depending upon a number of factors, including the types and molecular weights of the particular molecules used and the desired end use application.

The crosslinked polymer compositions can also be prepared to contain various imaging agents such as iodine or barium sulfate, or fluorine, in order to aid visualization of the compositions after administration via X-ray, or $^{19}$F-MRI, and the like.

Administration of the Crosslinked Synthetic Polymer Compositions

The compositions of the present disclosure may be administered before, during or after crosslinking of the branched polyamine and the hydrogel precursor. Certain uses, which are discussed in greater detail below, such as tissue augmentation, may require the compositions to be crosslinked before administration, whereas other applications, such as tissue adhesion, may allow for the compositions to be administered before crosslinking has reached "equilibrium." As used herein, the point at which crosslinking has reached equilibrium is the point at which the composition no longer feels tacky or sticky to the touch.

In order to administer the composition prior to crosslinking, the branched polyamine and the hydrogel precursor may be contained within separate barrels of a dual-compartment syringe. In this case, the two components do not actually mix until the point at which the two components are extruded from the tip of the syringe needle into the patient's tissue. This allows the vast majority of the crosslinking reaction to occur in situ, avoiding the problem of needle blockage which may occur if the two components are mixed too early and crosslinking between the two components is already too advanced prior to delivery from the syringe needle. The use of a dual-compartment syringe may allow for the use of smaller diameter needles, which may be advantageous when performing soft tissue augmentation.

Alternatively, the branched polyamine and the hydrogel precursor may be mixed prior to delivery to the tissue site, then injected to the desired tissue site immediately following mixing.

In another embodiment, the branched polyamine and the hydrogel precursor may be mixed, then extruded and allowed to crosslink into a sheet or other solid form. The crosslinked solid is then dehydrated to remove substantially all unbound water. The resulting dried solid may be ground or comminuted into particulates, then suspended in a nonaqueous fluid carrier, including, without limitation, hyaluronic acid, dextran sulfate, dextran, succinylated noncrosslinked collagen, methylated noncrosslinked collagen, glycogen, glycerol, dextrose, maltose, triglycerides of fatty acids (such as corn oil, soybean oil, and sesame oil), and egg yolk phospholipid. The suspension of particulates can be injected through a small-gauge needle to a tissue site. Once inside the tissue, the crosslinked polymer particulates will rehydrate and swell in size at least five-fold.

Use of the Crosslinked Polymers as Bioadhesives

Crosslinked polymers produced in accordance with the present disclosure may also be utilized as bioadhesives, for example, for use in surgery. As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and a non-native tissue surface or a surface of a synthetic implant.

In a general method for effecting the attachment of a first surface to a second surface, the branched polyamine and the hydrogel precursor are applied to a first surface, then the first surface is contacted with a second surface to effect adhesion between the first surface and the second surface. In embodiments, the branched polyamine and hydrogel precursor are first mixed to initiate crosslinking, then delivered to a first surface before substantial crosslinking has occurred between the nucleophilic groups on the branched polyamine and the electrophilic groups on the hydrogel precursor. The first surface is then contacted with the second surface to effect adhesion between the two surfaces. At least one of the first and second surfaces may be a native tissue surface.

For example, the branched polyamine and hydrogel precursor may be provided in separate syringes, the contents of which are then mixed together using syringe-to-syringe mixing techniques just prior to delivery to a first surface. As crosslinking between the corresponding reactive groups on the two components is generally initiated during the mixing process, it is important to deliver the reaction mixture to the first surface as soon as possible after mixing.

The reaction mixture can be extruded onto the first surface from the opening of a syringe or other appropriate extrusion device. Following application, the extruded reaction mixture can be spread over the first surface using a spatula, if necessary. Alternatively, the branched polyamine and the hydrogel precursor can be mixed together in an appropriate mixing dish or vessel, then applied to the first surface using a spatula.

In another method for preparing the reaction mixture, the branched polyamine and hydrogel precursor may be contained in separate chambers of a spray can or bottle with a nozzle, or other appropriate spraying device. In this scenario, the two components do not actually mix until they are expelled together from the nozzle of the spraying device. Following application of the reaction mixture to a surface, in embodiments tissue containing collagen, the first surface is contacted with a second surface. If the two surfaces are contacted before substantial crosslinking has occurred between the two components, the reactive groups on the two components will also covalently bond with primary amino groups on lysine residues of collagen molecules present on either or both of the surfaces, providing improved adhesion.

The two surfaces may be held together manually, or using other appropriate means, while the crosslinking reaction is proceeding to completion. Crosslinking should be complete within about 30 seconds to about 10 minutes after mixing of the branched polyamine and hydrogel precursor. However, the time required for complete crosslinking to occur is dependent on a number of factors, including the types and molecular weights of the two components and, in embodiments, the concentrations of the two components (i.e., higher concentrations result in faster, i.e., shorter, crosslinking times).

At least one of the first and second surfaces may be a native tissue surface. As used herein, the term "native tissue" refers to biological tissues that are native to the body of the specific patient being treated. As used herein, the term "native tissue" is intended to include biological tissues that have been elevated or removed from one part of the body of a patient for implantation to another part of the body of the same patient (such as bone autografts, skin flap autografts, etc.). For example, the compositions of the present disclosure can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants). For example, the crosslinked polymer compositions of the present disclosure can be used to adhere a donor cornea to the eye of a recipient patient.

As used herein, the term "synthetic implant" refers to any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

In embodiments, the branched polyamine may be applied to one surface, for example tissue or an implant, while the hydrogel precursor is applied to a second surface, similarly tissue or an implant. The first surface and second surface may then be brought into contact with each other so that the branched polyamine on the first surface reacts with the hydrogel precursor on the second surface, thereby forming a composition of the present disclosure capable of adhering the two surfaces together.

Use of Crosslinked Polymer Compositions in Tissue Augmentation

The crosslinked polymer compositions of the present disclosure can also be used for augmentation of soft or hard tissue within the body of a mammalian subject. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue.

The compositions of the present disclosure may be used as a replacement material for synovial fluid in osteoarthritic joints, where the crosslinked polymer compositions serve to reduce joint pain and improve joint function by restoring a soft hydrogel network in the joint. The crosslinked polymer compositions can also be used as a replacement material for the nucleus pulposus of a damaged intervertebral disk. As such, the nucleus pulposus of the damaged disk is first removed, then the crosslinked polymer composition is injected or otherwise introduced into the center of the disk. The composition may either be crosslinked prior to introduction into the disk, or allowed to crosslink in situ.

In a general method for effecting augmentation of tissue within the body of a mammalian subject, the branched polyamine and the hydrogel precursor may be simultaneously injected to a tissue site in need of augmentation through a small-gauge (e.g., 25-32 gauge) needle. Once inside the patient's body, the nucleophilic groups on the branched polyamine and the electrophilic groups on the hydrogel precursor will react with each other to form a crosslinked polymer network in situ. Electrophilic groups on the bydrogel precursor may also react with primary amino groups on lysine residues of collagen molecules within the patient's own tissue, providing for "biological anchoring" of the compositions with the host tissue.

Use of the Crosslinked Polymer Compositions to Prevent Adhesions

Another use of the crosslinked polymer compositions of the present disclosure is to coat tissues in order to prevent the formation of adhesions following surgery or injury to internal tissues or organs. In a general method for coating tissues to prevent the formation of adhesions following surgery, the branched polyamine and hydrogel precursors are mixed, then a thin layer of the reaction mixture is applied to the tissues comprising, surrounding, and/or adjacent to the surgical site before substantial crosslinking has occurred between the nucleophilic groups on the branched polyamine and the electrophilic groups on the hydrogel precursor. Application of the reaction mixture to the tissue site may be by extrusion, brushing, spraying (as described above), or by any other convenient means.

Following application of the reaction mixture to the surgical site, crosslinking is allowed to continue in situ prior to closure of the surgical incision. Once crosslinking has reached equilibrium, tissues which are brought into contact with the coated tissues will not stick to the coated tissues. At this point in time, the surgical site can be closed using conventional means (sutures, staples, clips, tacks, etc.).

In general, compositions that achieve complete crosslinking within a relatively short period of time (in embodiments from about 5 minutes to about 15 minutes following mixture of the branched polyamine and the hydrogel precursor) may be desirable for use in the prevention of surgical adhesions, so that the surgical site may be closed relatively soon after completion of the surgical procedure.

Use of the Crosslinked Polymers to Coat Implants

Another use of the crosslinked polymer compositions of the present disclosure is as a coating material for synthetic implants. In a general method for coating a surface of a synthetic implant, the two components are mixed, then a thin layer of the reaction mixture is applied to a surface of the implant before substantial crosslinking has occurred between the nucleophilic groups on the branched polyamine and the electrophilic groups on the hydrogel precursor. Application of the reaction mixture to the implant surface may be by extrusion, brushing, spraying (as described above), or by any other convenient means. Following application of the reaction mixture to the implant surface, crosslinking is allowed to continue until complete crosslinking has been achieved.

Although this method can be used to coat the surface of any type of synthetic implant, it may be useful for implants where reduced thrombogenicity is an important consideration, such as artificial blood vessels and heart valves, vascular grafts, vascular stents, and stent/graft combinations. The method may also be used to coat implantable surgical devices or membranes (e.g., monofilament polypropylene) or meshes (e.g., for use in hernia repair). Breast implants may also be coated using the above method in order to minimize capsular contracture.

The compositions of the present disclosure may also be used to coat lenticules, which are made from either naturally occurring or synthetic polymers.

Use of the Crosslinked Polymers to Treat Aneurism

The crosslinked polymer compositions of the present disclosure can be extruded or molded in the shape of a string or coil, then dehydrated. The resulting dehydrated string or coil can be delivered via catheter to the site of a vascular malformation, such as an aneurysm, for the purpose of vascular occlusion and, ultimately, repair of the malformation. The dehydrated string or coil can be delivered in a compact size and will rehydrate inside the blood vessel, swelling several times in size compared to its dehydrated state, while maintaining its original shape.

Use of Crosslinked Polymers to Deliver Biologically Active Agents

The crosslinked polymer compositions of the present disclosure may also be used for localized delivery of various drugs and other biologically active agents, sometimes referred to herein as "bioactive agents." The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of bioactive agents which may be utilized in compositions in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the composition in accordance with the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the compositions.

Other bioactive agents which may be included in a composition in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticopvulsants; antidepressants; antihistamines; and immunological agents.

Other examples of suitable bioactive agents which may be included in the composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

A single bioactive agent may be utilized in the composition or, in alternate embodiments, any combination of bioactive agents may be utilized in the compositions of the present disclosure.

Biologically active agents may be incorporated into the crosslinked polymer composition by admixture. Alternatively, the agents may be incorporated into the crosslinked polymer matrix, as described above, by binding these agents with functional groups on the hydrogel precursors. Such compositions may include linkages that can be easily biodegraded, for example as a result of enzymatic degradation, resulting in the release of the active agent into the target tissue, where it will exert its desired therapeutic effect.

The type and amount of active agent used will depend, among other factors, on the particular site and condition to be treated and the biological activity and pharmacokinetics of the active agent selected.

Use of Crosslinked Polymers to Deliver Cells or Genes

The crosslinked polymer compositions of the present disclosure can also be used to deliver various types of living cells or genes to a desired site of administration in order to form new tissue. The term "genes" as used herein is intended to encompass genetic material from natural sources, synthetic nucleic acids, DNA, antisense-DNA and RNA.

When used to deliver cells, for example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

Other Uses for the Crosslinked Polymers

The crosslinked polymer compositions of the present disclosure can be used to block or fill various lumens and voids in the body of a mammalian subject. The compositions can also be used as biosealants to seal fissures or crevices within a tissue or structure (such as a vessel), or junctures between adjacent tissues or structures, to prevent leakage of blood or other biological fluids.

The crosslinked polymer compositions of the present disclosure can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture may be applied to the interior surface of the vessel (for example, via catheter) immediately following mixing of the two components. Because the compositions of the present disclosure are not readily degradable in vivo, the potential for restenosis due to degradation of the coating is minimized.

The following Example is being submitted to illustrate embodiments of the present disclosure. This Example is intended to be illustrative only and is not intended to limit the scope of the present disclosure. Also, parts and percentages are by weight unless otherwise indicated. As used herein, "room temperature" refers to a temperature of from about 20° C. to about 25° C.

EXAMPLE 1

Production of branched polyamine. About 21.77 grams of p-nitrophenoxyacetic acid was dissolved in about 80.00 ml of tetrahydrofuran. Approximately 21.02 grams of oxalyl chloride $(COCl)_2$ was added to the solution followed by the addition of about two drops of dimethylformamide. The solution was stirred at room temperature for a period of from about 1 hour to about 2 hours. The stirred solution was evaporated to dryness, the residue was dissolved in THF and mixed with about 20 grams of pentaerythritol ethoxylate. The resulting solution was then stirred and heated at about 65° C. for about 18 hours. The nitrophenoxyacetyl ester thus produced was analyzed, and its presence confirmed by, $^1$H NMR.

About 38 grams of the nitrophenoxyacetyl ester was then dissolved in about 150 ml of tetrahydrofuran. Approximately 2.14 grams of Palladium on Carbon (10% Pd) was added to the solution along with about 31.68 grams of ammonium formate $(HCO_2NH_4)$. The solution was then heated at about 60° C. overnight. The reaction mixture was filtered over CELITE® and evaporated. The residue, which was the branched polyamine, was analyzed and its presence confirmed by $^1$H NMR.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A process comprising:
reacting a branched polyol with a nitroaryl carboxylic acid to form a nitrobenzoyl ester;
hydrogenating the nitrobenzoyl ester to form a branched polyamine, and
reacting the branched polyamine with a N-protected amino acid to form a protected polyamine, wherein the N-protected amino acid is selected from the group consisting of:

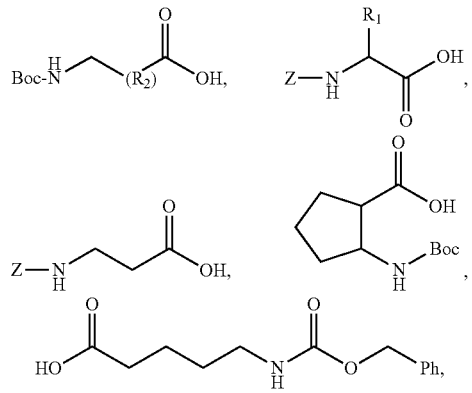

-continued

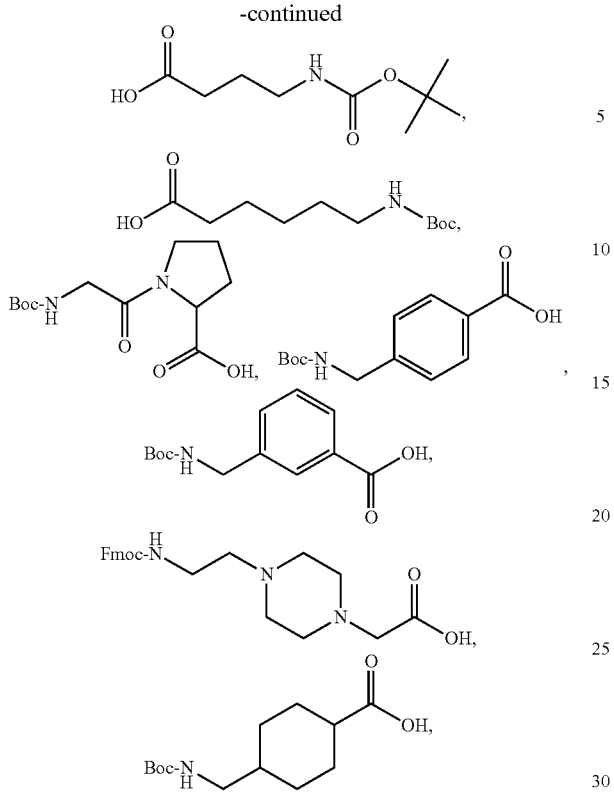

and combinations thereof wherein $R_1$ is selected from the group consisting of alkyl, aryl, heteroaryl, and cycloalkyl, $R_2$ is selected from the group consisting of $CH_2$, alkyl, alkoxy, and combinations thereof, and Z is selected from the group consisting of tert-butoxycarbonyl, benzyloxycarbonyl, and fluorenylmethyoxycarbonyl.

2. The process as in claim 1, wherein at least one of the branches of the branched polyol includes an alkoxy group.

3. The process as in claim 1, wherein the branched polyol is a branched pentaerythritol.

4. The process as in claim 1, wherein the branched polyol is selected from the group consisting of pentaerythritol ethoxylate, pentaerythritol propoxylate, trimethylolpropane, dipentaerythritol, tripentaerythritol, and combinations thereof.

5. The process as in claim 1, wherein the nitroaryl-carboxylic acid is selected from the group consisting of 3-nitrobenzoic acid, p-nitrophenoxyacetic acid, m-nitrophenoxyacetic acid, o-phenyl acetic acid, m-phenyl acetic acid, p-phenyl acetic acid, m,p-nitrocinnamyl acid, benzoic acid, 4-nitrobenzoic acid, and combinations thereof.

6. The process as in claim 1, wherein the hydrogenating step includes mixing the nitrobenzoyl ester with a platinum group catalyst.

7. The process as in claim 6, wherein the platinum group catalyst includes a metal selected from the group consisting of platinum, palladium, rhodium and ruthenium.

8. The process as in claim 1, further comprising contacting the protected polyamine with an acid selected from the group consisting of trifluoroacetic acid (TFA), HCl in dioxane, and combinations thereof.

9. A process comprising:
reacting a branched polyol with a nitroaryl carboxylic acid to form a nitrobenzoyl ester;
reducing the nitrobenzoyl ester with a catalyst to form a branched polyamine, and
reacting the branched polyamine with an N-protected amino acid to form a protected polyamine, wherein the N-protected amino acid is selected from the group consisting of:

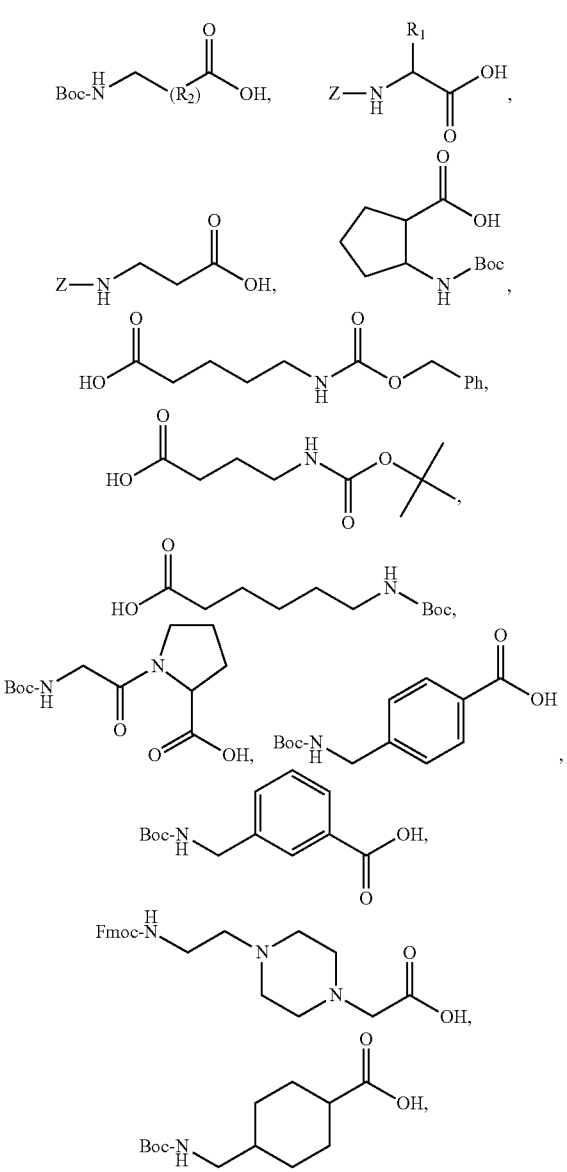

and combinations thereof wherein $R_1$ is selected from the group consisting of alkyl, aryl, heteroaryl, and cycloalkyl, $R_2$ is selected from the group consisting of $CH_2$, alkyl, alkoxy, and combinations thereof, and Z is selected from the group consisting of tert-butoxycarbonyl, benzyloxycarbonyl, and fluorenylmethyoxycarbonyl.

10. The process as in claim 9, wherein at least one of the branches of the branched polyol includes a hydroxyester group.

11. The process as in claim 9, wherein the branched pentaerythritol is selected from the group consisting of pentaerythritol ethoxylate, pentaerythritol propoxylate, pentaerythritol butoxylate, and pentaerythritol pentoxylate.

12. The process as in claim 9, wherein the nitroaryl carboxylic acid is p-nitrophenoxyacetic acid.

13. The process as in claim 9, wherein the catalyst is a platinum group catalyst including a metal selected from the group consisting of platinum, palladium, rhodium and ruthenium.

14. The process as in claim 9, further comprising contacting the protected polyamine with an acid selected from the group consisting of trifluoroacetic acid (TFA), HCl in dioxane, and combinations thereof.

15. A process comprising:
reacting a branched polyol with a nitroaryl carboxylic acid to form a nitrobenzoyl ester;
hydrogenating the nitrobenzoyl ester to form a branched polyamine;
reacting the branched polyamine with an N-protected amino acid to form a protected polyamine, wherein the N-protected amino acid is selected from the group consisting of:

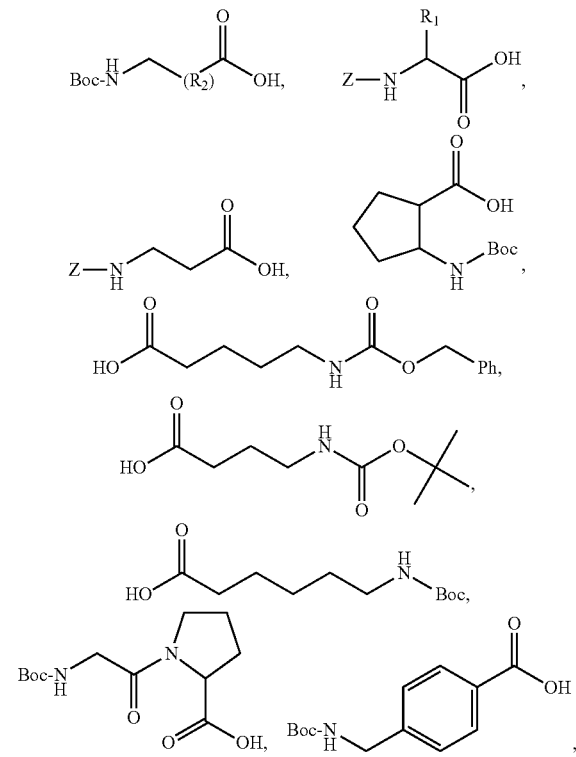

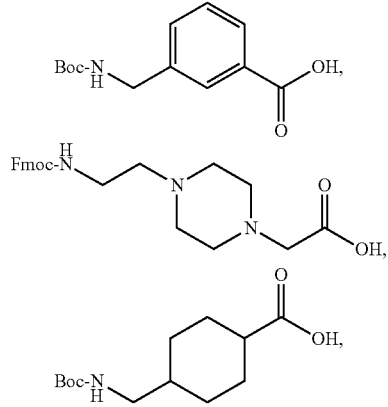

and combinations thereof wherein $R_1$ is selected from the group consisting of alkyl, aryl, heteroaryl, and cycloalkyl, $R_2$ is selected from the group consisting of $CH_2$, alkyl, alkoxy, and combinations thereof, and Z is selected from the group consisting of tert-butoxycarbonyl, benzyloxycarbonyl, and fluorenylmethyoxycarbonyl, deprotecting the protected polyamine with an acid selected from the group consisting of trifluoroacetic acid (TFA), HCl in dioxane, and combinations thereof; and reacting the deprotected branched polyamine with a hydrogel precursor.

16. The process as in claim 15, wherein the hydrogel precursor includes at least one electrophilic functional group.

17. The process as in claim 15, wherein at least one of the branches of the branched polyol includes an alkoxy group.

18. The process as in claim 15, wherein the branched polyol comprises a branched pentaerythritol.

19. The process as in claim 15, wherein the branched pentaerythritol is selected from the group consisting of pentaerythritol ethoxylate, pentaerythritol propoxylate, pentaerythritol butoxylate, and pentaerythritol pentoxylate.

20. The process as in claim 15, wherein the nitroaryl carboxylic acid comprises p-nitrophenoxyacetic acid.

21. The process as in claim 15, wherein the hydrogenating step includes contacting the nitrobenzoyl ester with a platinum group catalyst.

22. The process as in claim 15, wherein the catalyst is a platinum group catalyst including a metal selected from the group consisting of platinum, palladium, rhodium and ruthenium.

* * * * *